United States Patent [19]
Brodeur et al.

[11] Patent Number: 6,115,127
[45] Date of Patent: Sep. 5, 2000

[54] NON-CONTACT MEASUREMENTS OF ULTRASONIC WAVES ON PAPER WEBS USING A PHOTOREFRACTIVE INTERFEROMETER

[75] Inventors: Pierre H. Brodeur, Smyrna; Emmanuel F. Lafond, Atlanta, both of Ga.

[73] Assignee: Institute of Paper Science and Technology, Atlanta, Ga.

[21] Appl. No.: 09/192,847

[22] Filed: Nov. 16, 1998

Related U.S. Application Data

[60] Provisional application No. 60/065,781, Nov. 17, 1997.

[51] Int. Cl.[7] ..................................................... G01B 9/02
[52] U.S. Cl. ........................................... 356/357; 356/432
[58] Field of Search ................................... 356/349, 342, 356/357, 432

[56] References Cited

U.S. PATENT DOCUMENTS 5,131,748  7/1992  Monchalin et al. .................... 356/349

*Primary Examiner*—Robert H. Kim
*Attorney, Agent, or Firm*—Fitch, Even, Tabin & Flannery

[57] ABSTRACT

An apparatus and method for non-contact measurement of ultrasonic waves on moving paper webs employs a photorefractive interferometer. The photorefractive interferometer employs an optical head in which the incident beam and reflected beam are coaxial, thus enabling detection of both in-plane and out-of-plane waves with a single apparatus. The incident beam and reference beams are focused into a line enabling greater power to be used without damaging the paper.

25 Claims, 13 Drawing Sheets

CYLINDRICAL PLANO-CONVEX   SPHERICAL PLANO-CONVEX   SPHERICAL MENISCUS

CYLINDRICAL PLANO-CONVEX   SPHERICAL PLANO-CONVEX   SPHERICAL MENISCUS

CYLINDRICAL PLANO-CONVEX   SPHERICAL PLANO-CONVEX   SPHERICAL MENISCUS

NON-CONTACT MEASUREMENTS OF ULTRASONIC WAVES ON PAPER WEBS USING A PHOTOREFRACTIVE INTERFEROMETER

CROSS REFERENCE TO RELATED APPLICATION

This application claims the benefit of U.S. Provisional Application No. 60/065,781, filed Nov. 17, 1997, which is incorporated herein by reference.

GOVERNMENT INTEREST

This invention was made with Government support under Contract No. DE-FC07-97ID13578 awarded by the Department of Energy. The Government has certain rights in this Invention.

FIELD OF THE INVENTION

This invention relates to the measurement of ultrasonic waves in paper webs, and more particularly to an apparatus and method for non-contact measurement of ultrasonic waves on static and moving paper products using a photorefractive interferometer.

BACKGROUND OF THE INVENTION

Measurement of the characteristics of a moving paper web is essential to the paper manufacturing process. A simple way to determine some of the mechanical properties of a material, such as a moving paper web, is to generate ultrasonic waves in the material at one location in a specimen and then to detect them at another point in the specimen at a given distance from the first location. The speeds of the ultrasonic waves along certain directions of the paper web will provide the rigidity tensor of the paper, which is related to the paper's mechanical properties. Numerous contact and non-contact measurement techniques exist and have varying degrees of success and application.

The direction of displacement of the surface of the paper caused by propagating ultrasonic waves is independent of the direction of propagation and can be in any direction in the plane of the paper (called in-plane displacements) and in any direction normal to it (out-of-plane displacements). By using a time base triggered at the instant of generation of the waves, the travel time between the generation and detection points can be measured. Using this travel time and if the precise distance between the generation and detection points is known, the speeds of the ultrasonic waves can be determined. The speeds of ultrasonic waves are related in a more or less simple way to some of the coefficients of the rigidity tensor of the paper, and thus are linked to some of the paper's mechanical properties. Measurements of the propagation speeds of specific ultrasonic waves by detecting both the in-plane and out-of-plane displacements can be used to evaluate some of the main mechanical properties of the paper and to control the paper machine.

Prior art methods of measurement of ultrasonic waves in various materials using laser interferometers can be found in the following references: "Broadband optical detection of ultrasound by two-wave mixing in a photorefractive crystal", R. K. Ing and J. P. Monchalin, Appl. Phys. Lett. Vol. 59, p. 3233–3235, 1991; "Detection of ultrasonic motion of a scattering surface by two-wave mixing in a photorefractive GaAs crystal", A. Blouin and J. P. Monchalin, Appl. Phys. Lett. vol. 65, number 8, August 1994; "Ultrasound detection on rough surfaces using heterodyne photorefractive interferometer: applications to NDE", R. K. Ing, D. Royer, Bruno F. Pouet and Sridhar Krishnaswamy, p. 681, 684, Proceedings of the 1996 IEEE Ultrasonics Symposium, San Antonio, Tex., November 1996; "Heterodyne interferometer with two-wave mixing in photorefractive crystals for ultrasound detection on rough surfaces", Bruno F. Pouet, R. K. Ing, Sridhar Krishnaswamy, D. Royer, Appl. Phys. Lett. Vol. 69, number 25, December 1996; "Paper stiffness monitoring using laser-ultrasonics", P. H. Brodeur, Y. H. Berthelot, M. A. Johnson, and J. P. Gerhardstein, Proc. 1996 IEEE Int. Ultrasonics Symp., San Antonio, Nov. 3–6, 1996; "Investigation of the mechanical properties of copy paper using laser generated and detected lamb waves", M. A. Johnson, Ph.D. Thesis, Georgia Inst. of Tech., 1996; and "Noncontact laser generation and detection of lamb waves in paper", P. H. Brodeur, M. A. Johnson, Y. H. Berthelot, and J. P. Gerhardstein, J. Pulp & Paper Sc. 23(5) J238–J243, 1997.

Several U.S. patents disclose techniques for measuring ultrasonic waves in materials in a non-contact way: U.S. Pat. No. 5,638,396, issued Jun. 10, 1997, to Klimek, entitled "Laser ultrasonics-based material analysis system and method;" U.S. Pat. No. 5,608,166, issued Mar. 4, 1997, to Monchalin and Blouin, entitled "Generation and detection of ultrasound with long pulse lasers;" U.S. Pat. No. 5,585,921, issued Dec. 17, 1996, to Pepper, et al., entitled "Laser-ultrasonic non-destructive, non-contacting inspection system;" U.S. Pat. No. 5,131,748, issued Jul. 21, 1992, to Monchalin and Ing, entitled "Broadband optical detection of transient motion from a scattering surface by two-wave mixing in a photorefractive crystal;" U.S. Pat. No. 5,025,665, issued Jun. 25, 1991, to Keyes IV and Thompson, entitled "Non-contacting on-line paper strength measuring system;" and U.S. Pat. No. 5,680,212, issued Oct. 21, 1997, to Blouin, et al., entitled "Sensitive and fast response optical detection of transient motion from a scattering surface by two-wave mixing."

Measuring the properties of a moving web of paper requires overcoming several problems. First, the very nature of paper makes it difficult to use optical techniques. Because of the surface roughness of paper (from many fibers) and the roughness of the fibers themselves, the light reflected from the surface is scattered almost isotropically in a half space (i.e., the paper surface becomes a Lambertian source). As a result, the incident beam is backscattered by the paper forming a speckled reflection. While the power collected by a lens centered in the direction of the incoming beam will stay small, as long as the solid angle of collected light stays small, the speckled nature of the reflection makes it very difficult for all types of interferometers, working with only a single speckle, even on static surfaces, to detect ultrasound.

Piezoelectric transducers have been used to generate and detect ultrasonic waves on moving paper but have the disadvantage of either being contact transducers which could damage the product, or in the case of air-coupled transducers, offering poor energy coupling into the material, and thus a weak signal. Several non-contact ways of generating ultrasonic waves in materials exist, such as, air-coupled transducers or time-gated microwaves. A recent technique called Laser Ultrasonics is an interesting alternative to the use of piezoelectric transducers.

In Laser Ultrasonics, ultrasound is generated in the paper using the thermoelastic effect, which consists of impinging the surface of the sample with a laser spot for a very short time duration. The sudden thermal dilatation created by the absorption of the laser light by the material generates ultrasonic waves propagating in the paper. The generation of ultrasonic waves by a laser has the advantage of being a fully non-contact method.

Lasers are also interesting tools for detecting ultrasonic waves when considering the time coherence properties of laser sources. Indeed, interferometers using laser sources have been used to detect the high frequency and small amplitude displacements of the surface of the paper caused by propagating ultrasonic waves. U.S. Pat. No. 5,814,730 describes use of a laser beam and the Doppler effect to measure the orthogonal displacement velocity of an acoustical wave to determine various characteristics of a paper web.

The most commonly used prior art interferometers for the detection of ultrasound are the knife-edge interferometer, the Mach-Zehnder interferometer, and the Fabry-Pérot interferometer. In each of these interferometers, the detection relates solely to the change of the properties of a laser beam by the ultrasound, so the detection is performed on the product without any contact.

Thus, appropriate generation and detection of ultrasonic waves are able to provide some of the mechanical properties of paper and by using laser, can be performed without any contact of any kind on the paper products.

While the above interferometers have been useful for measuring properties of static paper products, they have, however, some significant disadvantages when used on a moving paper web. Paper is an optically highly scattering material. The Mach-Zehnder and knife-edge interferometers have a small étendue (throughput), and thus, are very sensitive to the change of laser speckle pattern caused by the fluttering of a paper web. Because these two interferometers work mainly with the specular reflection of laser light, it is expected that the reflected beam carrying the ultrasonic information would be unstable, when impinging fast moving paper. Thus, most single speckle interferometers such as Mach-Zehnder, Michelson, Sagnac, polarimetric and self-mixing interferometers need to use special, intricate and delicate devices such as a scanning mirror, time triggering of the ultrasound generation, etc. to detect ultrasound on surfaces that scatter light a lot such as paper. However these solutions provide new problems: having to use moving parts and the sensitivity of the mirror to vibrations. So these interferometers are not really acceptable for moving paper webs.

The Fabry-Pérot interferometer provides the advantage of having a large étendue, and thus is able to work on very scattering surfaces and on materials moving at a high speed. Unfortunately, its bandwidth provides an acceptable sensitivity only for frequencies above 1–2 MHz. The frequencies of the ultrasonic waves traveling in paper are typically in the range of 20 kHz to 2 MHz, due to paper's properties as an attenuating lowpass filter. Thus, when used on moving paper products, none of the above interferometers would be really satisfactory.

There is a need for a non-contact system and method of measuring ultrasonic waves on a moving paper web. There is a need for a system and method employing an interferometer with high étendue. There is also a need for a system and method which can measure both in-plane and out-of-plane displacements. There is a need for a system and method of measuring ultrasonic waves on a moving paper web in real time.

SUMMARY OF THE INVENTION

The apparatus and method embodying the invention provide non-contact, real-time detection of ultrasonic waves propagating in a moving paper web. The apparatus and method embodying the invention provide a photorefractive interferometer having a unique optical head which enables collection of both in-plane and out-of-plane ultrasonic waves from a moving paper web in a single apparatus. The apparatus and method of the invention employ a photorefractive interferometer for the on-line monitoring of ultrasonic waves on a paper web.

A photorefractive material is one in which its refractive index changes in response to light of low intensity. A photorefractive interferometer is an interferometer that employs a photorefractive crystal in order to have two or more beams of coherent light (usually laser beams) interfering in the crystal. The photorefractive interferometer can be a two-wave mixing (TWM) interferometer, a photoinduced-electromotive force (photo-EMF) interferometer, a four-wave mixing interferometer (FWM) or another type of wave-mixing interferometer.

The photorefractive interferometers considered here have a photorefractive crystal and are configured to provide preferably, two-wave mixing (TWM) or photo-induced electromotive force (photo-EMF). A photorefractive interferometer is particularly useful in the case of materials having a changing speckle pattern such as paper webs when they are impinged by coherent light (laser beams). In most cases, the photorefractive interferometer can adapt to the changing speckle pattern and still produce efficient interference in the crystal. The two types of photorefractive interferometer (TWM and photo-EMF) are preferred, since, among photorefractive interferometers, they provide the fastest adaptation to a quickly changing speckle pattern such as the one coming from a fast moving paper web. A photorefractive interferometer can also be called a multiple speckle interferometer. Fabry-Pérot or time delay interferometers are also multiple speckle interferometers, but they are not photorefractive interferometers since they do not have a photorefractive crystal. Since it is a multiple speckle interferometer, a photorefractive interferometer can collect a lot of speckles and thus a lot of the light backscattered from the paper (high throughput). The sensitivity of an interferometer depends mainly on the power of the collected light, hence a photorefractive interferometer will have a very good sensitivity compared to single speckle interferometers.

A preferred configuration of the invention is a two-wave mixing photorefractive interferometer. The principle of the use of a photorefractive crystal in a two-wave mixing interferometer is primarily that of a speckle adaptive interferometer. It allows the transfer of energy from a pump beam to a reference beam having the same speckle pattern as the one of the signal beam due to the diffraction of the pump beam into a reference beam caused by the grating formed by the interferences between the signal (reflected) and pump beam inside the photorefractive material. This configuration is particularly useful for a two-wave mixing interferometer because it provides adaptation of the wavefront of the reference beam to the one of the speckled signal beam (the beam reflected from the surface of the material) before they interfere. In principle, each speckle is matched with another one. Thus, the photorefractive crystal adapts the wavefronts of the reference beam and the reflected beam, then allows the beams to interfere. If a photodiode is used to convert the optical signal to an electrical signal, the adapted reference beam and reflected beam also interfere in the photodiode.

The photorefractive interferometer employed in the invention can be used for ultrasound detection on a static paper web, coated or uncoated, and on a paper sheet, coated or uncoated. Ultrasonic waves can be detected in many different types of moving paper webs using the invention. For example, moving paper webs of lightweight paper such as copy paper, newsprint, tissue paper and raw stock may be used. Heavy grade papers such as brown linerboard and bleachboard can also be used.

The photorefractive interferometer of the invention is particularly effective in detecting ultrasonic waves in moving paper webs. When detecting ultrasound in a static material, the photorefractive interferometer loses some of its advantage compared to other single speckle interferometers. In a static material the speckle pattern is not changing so there is no need for the interferometer to adapt to the changing speckle pattern.

The photorefractive interferometer provides an incident beam at one location on the material and a pump beam, collects the speckle light spot on the paper at the same location, then detects the interference between the reference beam and the collected (signal) beam. The interference is detected by one or more photodiodes which generate an electrical signal related thereto (TWM). In the case of a photo-EMF photorefractive interferometer, the interference of the two waves in the crystal is detected by electrodes placed on the crystal and converted to an electrical signal.

The detection laser may be focused as a point or other shape. Preferably the detection laser beam is focused onto a detection spot in the shape of a line on the paper. A cylindrical lens may be used to focus the detection spot into the shape of a line. When the detection spot is a line, preferably the generation spot is also focused into the shape of a line. A separate cylindrical lens may be used to focus the generation spot into the shape of a line. Preferably, the line is from 1 to 15 millimeters in length. An advantage of line focusing of the detection region is that the optical power impinging the moving or non-moving paper can be increased without damaging it. Using this configuration, the interferometer is sensitive to ultrasonic waves propagating along a direction perpendicular to the line for the line detection configuration and in any direction for a point detection configuration.

The line detection configuration is especially advantageous for use on static linerboard where the damage threshold and the collected power are very small giving a poor signal to noise ratio (impossible to put too much power on the paper without burning it).

The photorefractive interferometer may employ a variety of photorefractive crystals, laser wavelengths; it may work with or without the use of a high voltage to the crystal; and it may have electrodes deposited on the crystal. Preferably, when used on a moving web, the photorefractive interferometer uses a semiconductor crystal with a short response time of the order of 1 to 10 microseconds. On a non-moving web, response time is of less importance.

The photorefractive interferometer employs a unique optical head. The optical head is configured such that the incident beam and reflected beams are substantially coaxial. Preferably the angle of incidence is around 45 degrees from the plane of the moving paper. In this way, both in-plane and out-of-plane waves can be detected with a single optical head. Both in-plane and out-of-plane waves are mixed in the same output signal. They have separate waveforms, which can be separated in time. The first phase shift in the collected or reflected beam is caused by in-plane waves. The second phase shift in the collected beam is caused by out-of-plane waves.

An optical head which is configured to have both the incident and reflected beams substantially coaxial is especially advantageous in detecting ultrasound in moving paper webs. A moving paper web can displace (web fluttering) up to plus or minus 5 millimeters. The typical ultrasound displacements are from 1 nanometer to 200 nanometers. Using a prior art optical head in which the incident and reflected beams are at an angle from one another could result in the reflected beam not impinging the photorefractive crystal, thus no interference would occur and the signal (reflected) beam would not impinge the surface of the photodiode.

The photorefractive interferometer may employ the same objective for focusing the detection laser beam and for collecting the backscattered light from the paper sheet or it may employ two different objectives. If the same objective is used, such as a cylindrical lens, preferably the collected backscattered light is redirected along a direction perpendicular to the incident beam by another objective before being provided to the surface of the photorefractive crystal to produce interference with the pump beam.

The photorefractive interferometer provides a broadband and "flat" sensitivity in the frequency domain and a good sensitivity to the low frequency waves generally encountered in paper products (20 kHz–2 MHz). The photorefractive interferometer works on surfaces which are optically very scattering, such as paper products and can work on optical surfaces having a small optical reflection coefficient compared to those of metals (brown linerboard, for example). The photorefractive interferometer has good sensitivity in the range 20 kHz up to 2 MHz and has the ability to detect an ultrasonic signal even on moving paper products having a rapidly changing speckle pattern. The photorefractive interferometer has the ability to detect both in-plane and out-of-plane displacements, by simply changing the angle between the coaxial incident and collected beams, and the normal to the paper surface, i.e., without having to have a different setup.

BRIEF DESCRIPTION OF THE DRAWINGS

FIGS. 12A–12D are measurements of laser generated waves travelling along the machine direction of copy paper using the photorefractive interferometer of FIG. 9; and.

DETAILED DESCRIPTION OF THE PREFERRED EMBODIMENT

An apparatus and method for non-contact measurement of ultrasonic waves on paper webs or paper sheets according to the invention uses a photorefractive interferometer for the detection of ultrasonic waves on a moving paper web. The photorefractive interferometer employs efficient optical heads for the direction and collection of light to and from the paper web.

Figure 3:
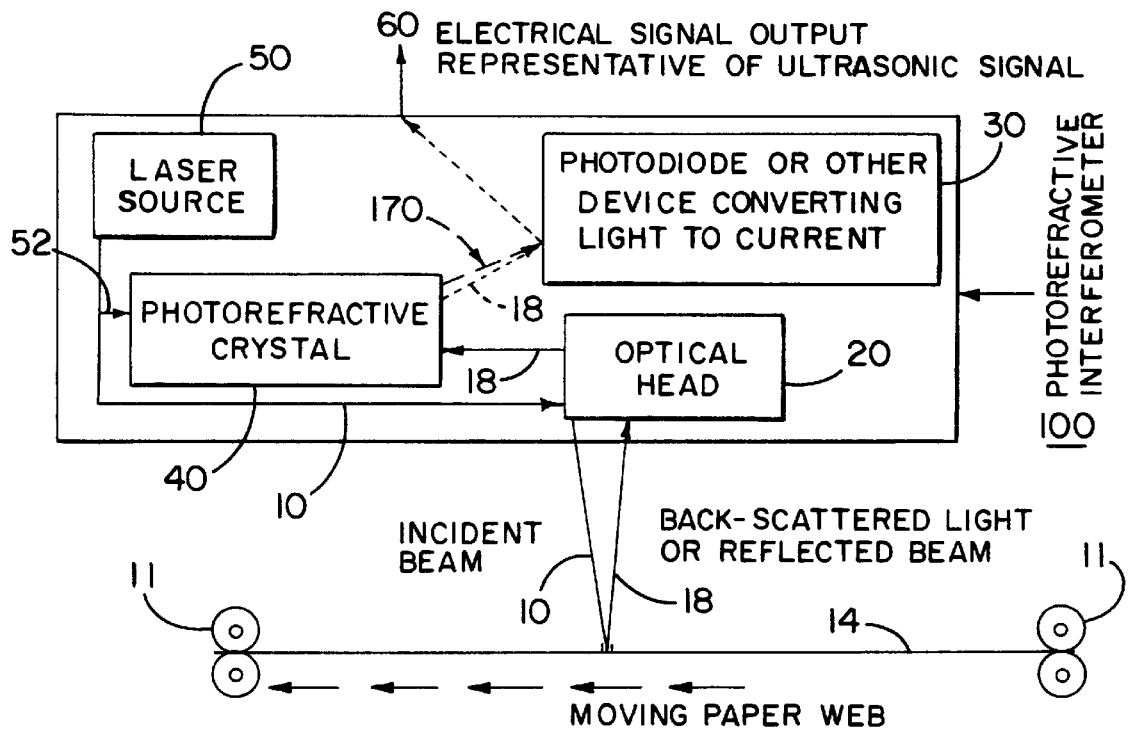
FIG. 3 is a schematic of an apparatus for non-contact measurement of ultrasonic waves in a moving paper web according to the invention.

Referring now to the drawings and especially to FIG. 3, an apparatus for non-contact measurement of ultrasonic waves on paper webs or paper sheets embodying the present invention is generally shown therein and referred to by reference numeral 100. Apparatus or photorefractive interferometer 100 includes optical head 20, photodiode 30, photorefractive crystal 40 and laser source 50. Laser source 50 generates a pump wave 52 which is provided to photorefractive crystal 40 and incident beam 10 which is provided to optical head 20. Optical head 20 transmits and focuses incident beam 10 onto moving paper web 14 (shown being moved by rollers 11) having ultrasonic waves propagating therein.

Backscattered light 18 is detected by optical head 20 where it is provided to photorefractive crystal 40. Incident beam 10 and reflected beam 18 are substantially coaxial. The pump wave 52 is combined with the backscattered light 18 in photorefractive crystal 40. The pump and backscattered waves interfere inside the photorefractive crystal 40 and create a grating in it. The grating diffracts the pump beam 52 into a reference beam 170 having a speckled wavefront matching the one of the backscattered beam. The part of the pump beam 52 which is not diffracted is blocked by a beam block 160 (see FIG. 9). The interferometric pattern from the ultrasonic waves in the moving web are detected by photodiode 30 which generates electrical signal 60 representative of the ultrasonic wave motion. Photodiode 30 may be any other device for converting light to an electrical signal.

The photorefractive interferometer 100 includes a laser source 50 emitting light 52 and 10 at a selected wavelength having a coherence length sufficient for use in interferometry. The selected wavelength is important for paper webs because the laser source is usually the most expensive part of the interferometer and its wavelength cannot be changed easily. The laser source 50 provides an incident beam 10 which is focused onto the paper. The material properties of the paper and the wavelength of the incident light affect the power of the backscattered light 18. The power of the backscattered light 18 impacts the strength of the signal generated by the interferometer 100 when the collected and reference beams interfere. The laser wavelength also determines what kind of photorefractive crystal will be used.

Several different wavelengths may be used for the detection laser, for example, 514.5 nm (Ar:Ion), 1064 nm (Nd:YAG), 532 nm (doubled Nd:YVO$_4$ or Nd:YAG), 780 nm and 852 nm (laser diode). The 514.5 nm and 1064 nm detection lasers have wavelengths with a high output power, which is useful for detection of ultrasonic waves on paper. The detection laser either can be pulsed (for example at a few hundreds of microseconds) or continuous wave (CW).

The photorefractive crystals 40 should have fast writing time of the grating and may be of the Sillenite type or semiconductor type. However, the response time should not be too short because if the grating inside the crystal adapts continuously and too quickly to the signal wavefront, the phase shift information (the ultrasonic signal) may be lost. Sillenite crystals include $Bi_{12}SiO_{20}$ (BSO), $Bi_{12}GeO_{20}$ (BGO), $Bi_{12}TiO_{20}$ (BTO), which all operate in the visible range (i.e., they are photorefractive and transparent). The Sillenite crystals are well suited for the Ar:Ion laser (514.5 nm) and lasers at 532 nm. The semiconductor type crystals, such as GaAs crystals, or InP:Fe, or CdTe:V must be used at infrared wavelengths for two wave mixing because they are not very absorbing in the range 950 nm to 1500 nm.

In a photoinduced-emf interferometer, the opposite effect is sought: total optical absorption of the beam by the crystal. GaAs:Cr is an example of a crystal which is efficient for the photoinduced-emf effect and can operate in the visible (514.5 or 532 nm) or in the near infrared (852 nm or lower).

Sillenite crystals are preferred for measurements on static paper products because of their high gain and resulting high signal-to-noise ratio. The response time for Sillenite crystals is generally not fast enough for adapting to the rapidly changing speckle pattern created by the displacement of a paper web under the incident beam. For measurements on moving paper, semiconductor crystals are preferred because of their short response time (typically from 1 to 10 microseconds). Semiconductor crystals have a smaller gain than Sillenite crystals, however, and thus a smaller signal-to-noise ratio than Sillenite crystals.

To overcome a small gain in a photorefractive crystal, a high voltage, which may be either DC or AC and may be pulsed or not, may be applied to the crystal at the moment when the ultrasonic waves are to be detected. The high voltage may be applied to either the Sillenite crystals or the semiconductor type crystals. The high voltage across the crystal provides two effects. First it moves more electrons from the bright fringes to the dark fringes of the interference patterns within the crystal and thus creates a stronger electric field grating. Second, it shifts the phase of the electric field closer to quadrature from the interference grating. Application of a high voltage must be carefully controlled, however, so as not to interfere with the adaptation of the crystal to the changing speckle pattern.

The sensitivity of the photorefractive interferometer 100 to ultrasonic displacement is directly related to the power of the light impinging the detector inside the interferometer. In the case of a TWM interferometer, the detector is a photodiode placed after the photorefractive crystal. In the case of a photo-EMF interferometer, the detector is the photorefractive crystal itself.

The unique configuration of the optical head 20 of the photorefractive interferometer is an important aspect of the invention. The optical head 20 can use a single or double objective to focus the incident beam 10 and collect the backscattered light 18 from the paper surface.

Since the optical head 20 in the photorefractive interferometer directs and collects light, its optimization will result in a global improvement of the signal to noise ratio and the sensitivity of the interferometer. Many different optical components, for example, lenses, mirrors, polarizers, can be used in the optical head 20.

Figure 4:
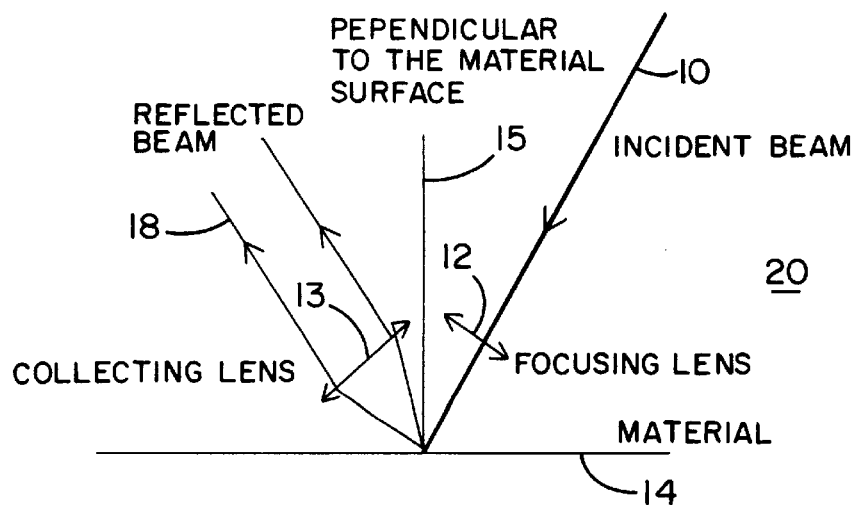
FIG. 4 is a schematic of a typical "V" type optical head.

A typical "V" type optical head, such as would be used in prior art photorefractive interferometers, is shown in FIG. 4. Optical head 20 includes focusing lens 12 for focusing incident beam 10 onto material 14 and collecting lens 13 for collecting the backscattered light and forming reflected beam 18. Focusing lens 12 and collecting lens 13 are disposed with respect to one another so that the path of the incident beam 10 and the collected bean 18 form a "V" shape.

Figure 2A:
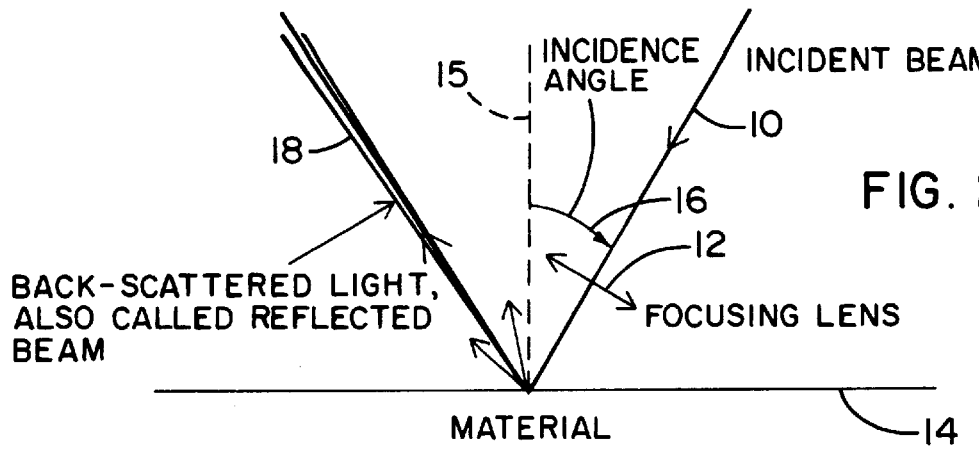
FIGS. 2A–2C are schematic of a typical distribution of reflected light from a non-scattering material for different angles of the incident beam.
Figure 2B:
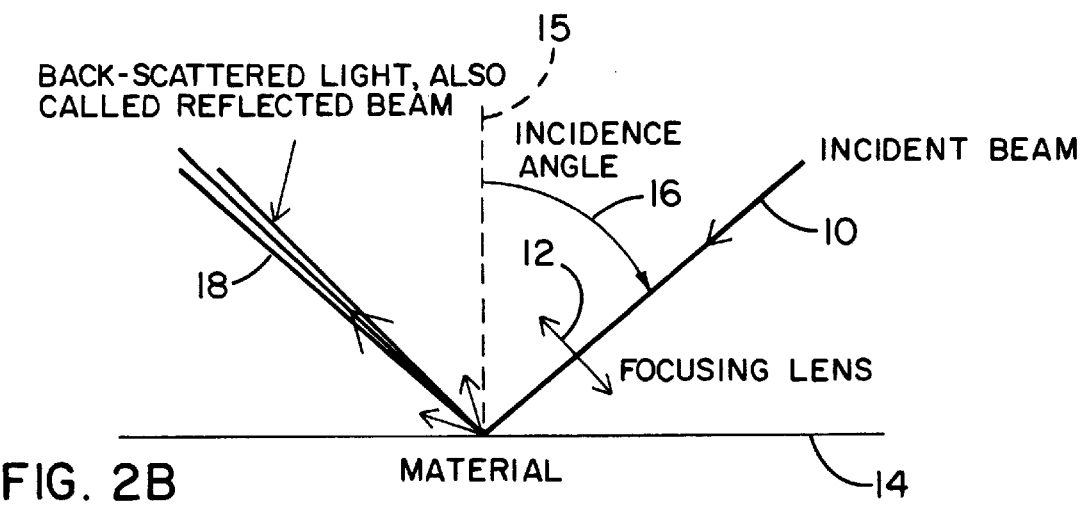
Figure 2C:
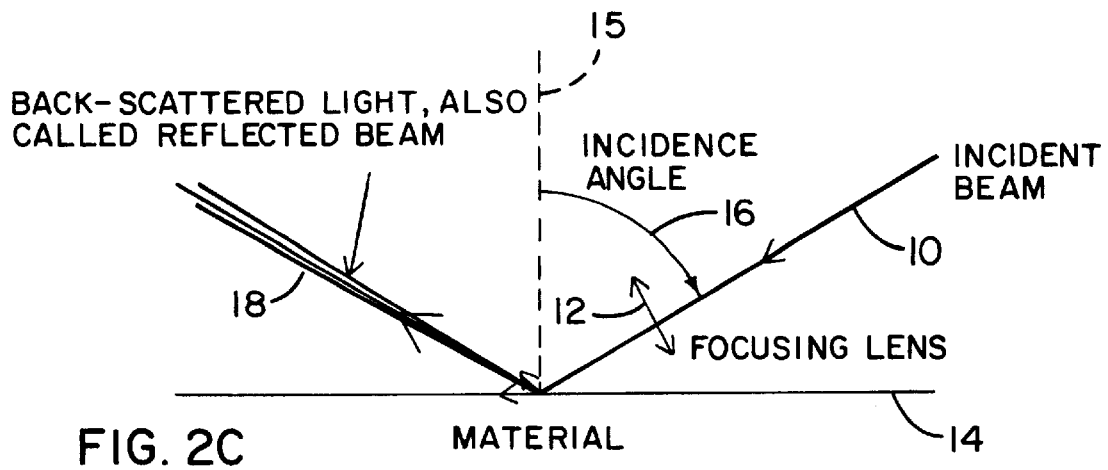

This prior art optical head has been used typically with relatively non-scattering materials such as metal sheet, metal parts, carbon-epoxy materials, plastic sheets or parts and many ceramic materials. Referring to FIGS. 2A–2C, it can be seen that for such materials, the backscattered light 18 does not vary much in beam shape with varying incidence angle 16 (the angle between the incidence beam and the perpendicular 15 to the material surface). As incidence angle 16 is increased from FIG. 2A to 2B to 2C, little change can be detected. The "V" shaped optical head supposes a reflected beam 18 having a distribution which is mainly centered around the mirror reflection angle (the same angle as the incident beam 10). The position of the collecting lens is thus optimized to be near that of the mirror reflection angle.

Figure 1A:
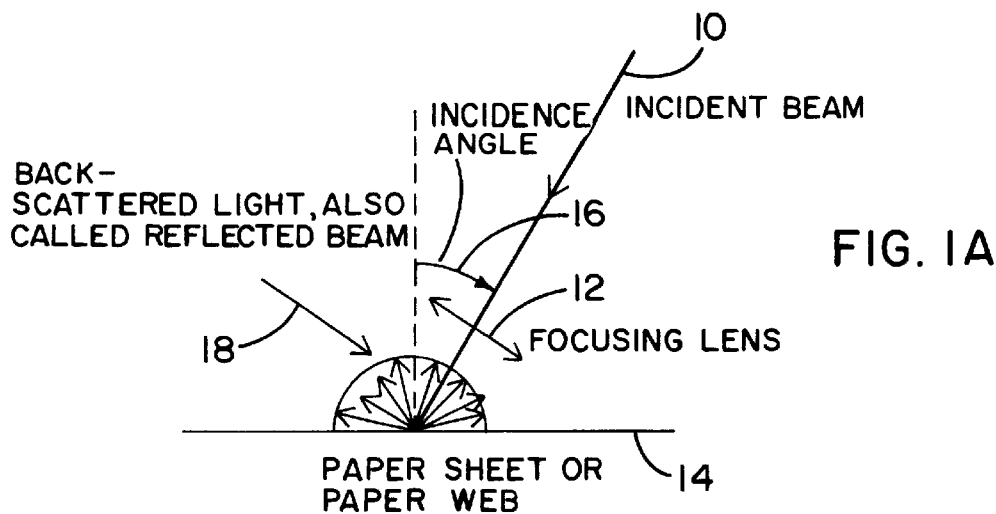
FIGS. 1A–1C are schematics of a typical distribution of backscattered light from an uncoated paper sheet or web for different angles of the incident beam.
Figure 1B:
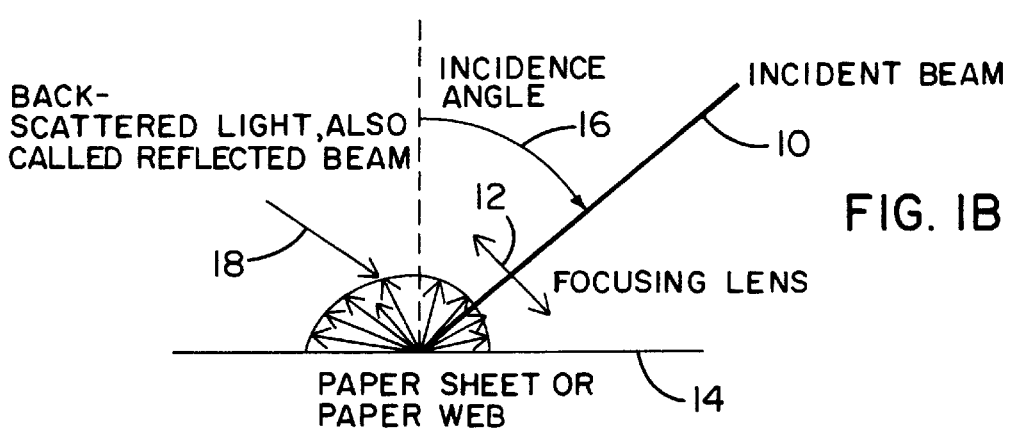
Figure 1C:
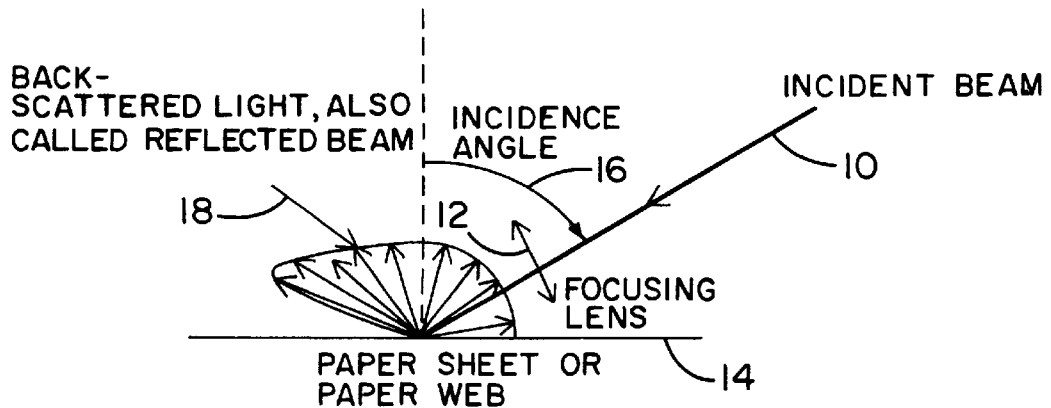

When the "V" shaped optical head has been used for detection of ultrasound in materials, however, due to the backscattering of light from a paper web, this optical head is not optimal. Referring to FIGS. 1A–1C, it can be seen that paper causes the backscattered light 18 to be backscattered almost isotropically in the half space above the paper. Thus the advantage of positioning the collection lens near the mirror reflection angle is no longer available. As incident angle 16 increases from FIG. 1A to 1B to 1C, the backscattering becomes more dispersed.

Another factor to consider in a moving paper web is if the paper moves vertically with respect to its position in one instant in time, the incident beam becomes not only unfocused on the paper web, but it is also translated along the web. Thus the position of the collecting lens is no longer optimum and the collected spot may not arrive at the photorefractive crystal 40. The fact that the paper may move vertically a few millimeters is not related to the propagation of ultrasonic waves traveling in it. This phenomenon is called fluttering and occurs frequently in paper mills on paper webs. The optical head 20, in which the incident beam and reflected beam are substantially coaxial overcomes the problems of fluttering.

Figure 5:
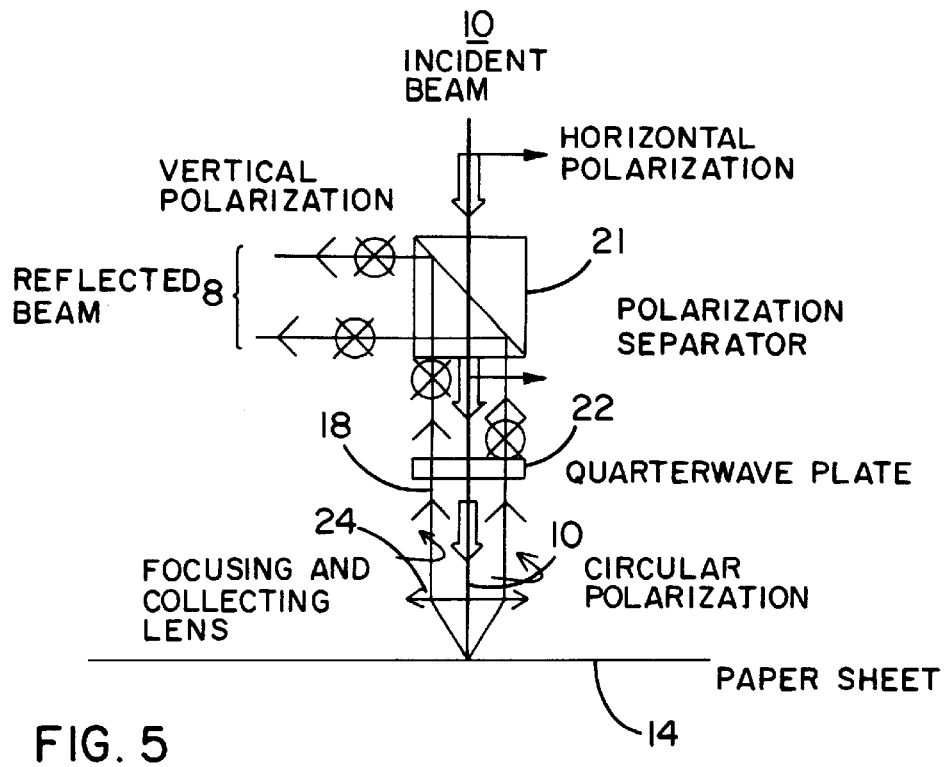
FIG. 5 is a schematic of a typical "T" type optical head with quarterwave plate.
Figure 6:
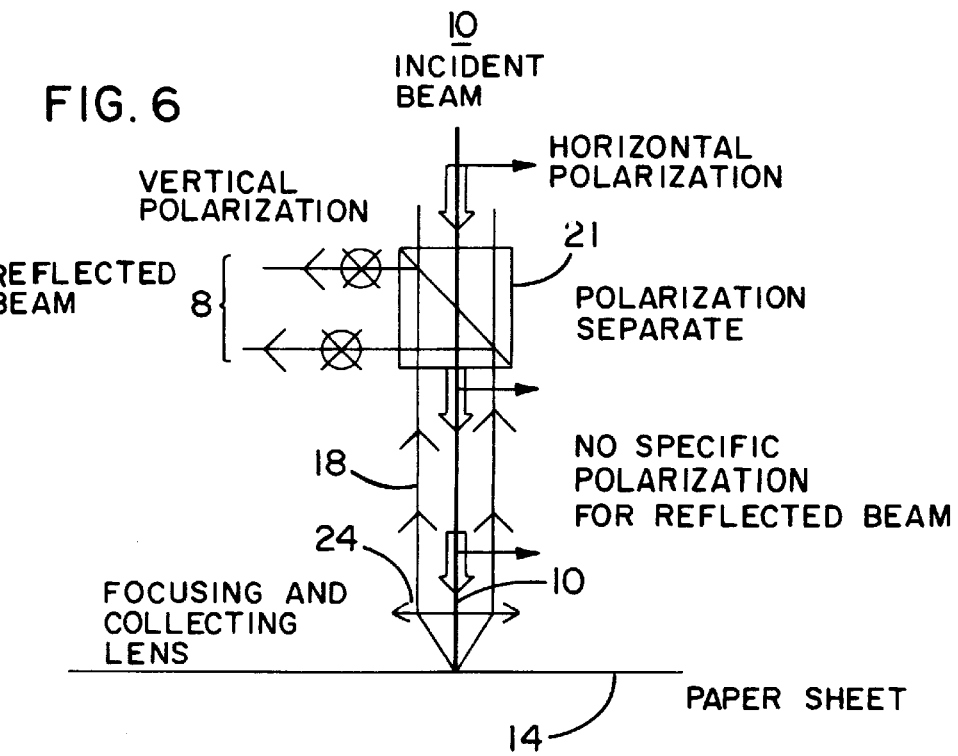
FIG. 6 is a schematic of a typical "T" type optical head without quarterwave plate.

Several optical heads in which the incident beam and reflected beams are substantially coaxial may be used. A preferred optical head 20 is a "T" shaped optical head, as shown in FIGS. 5 and 6. Incident beam 10 is linearly polarized in such a direction that it goes through the polarization separator 21 without being attenuated. Polarization separator 21 is preferably a polarizing cube beamsplitter. Then it arrives on quarterwave plate 22 which has to be properly oriented in such a way that the beam becomes circularly polarized after going through it.

Focusing and collecting lens 24 is preferably a non-polarizing material such as a plano-convex or meniscus lens made of glass. Focusing and collecting lens 24 can be cylindrical or spherical. Focusing and collecting lens 24 focuses beam 10 onto the paper web 14, then it collects and collimates the reflected beam 18. After beam 18 passes through quarterwave plate 22, the beam is linearly polarized perpendicular to the direction of incident beam 10. Thus, beam 18 is reflected off the polarization separator 21 and can be directed onto the photorefractive crystal 40.

In this preferred embodiment of the optical head 20, the incident beam 10 is coaxial with the reflected beam 18. So, if the paper moves vertically (fluttering), the position of the incident spot on the paper web 14 does not change. Also, if the depth of focus of the focusing and collecting lens 24 is large enough, with this configuration, the beam stays collimated. It should be noted that this configuration assumes that the paper does not depolarize the incident beam after reflection, which may be true for glossy paper. However, most paper grades are uncoated and thus depolarize light (i.e., the backscattered light does not have the same polarization as the incoming beam). For such papers, the optical head 20 shown in FIG. 6 is preferred.

Optical head 20 as shown in FIG. 6 is the same as optical head 20 in FIG. 5 with the omission of quarterwave plate 22. In FIG. 6, incident beam 10 still has a linear polarization when it arrives at the surface of paper sheet 14 because the quarterwave plate 22 has been removed. The light backscattered by this paper is partially or totally depolarized so only the speckles having a polarization perpendicular to the incoming beam 10 will be reflected towards the photorefractive crystal 40.

Figure 7:
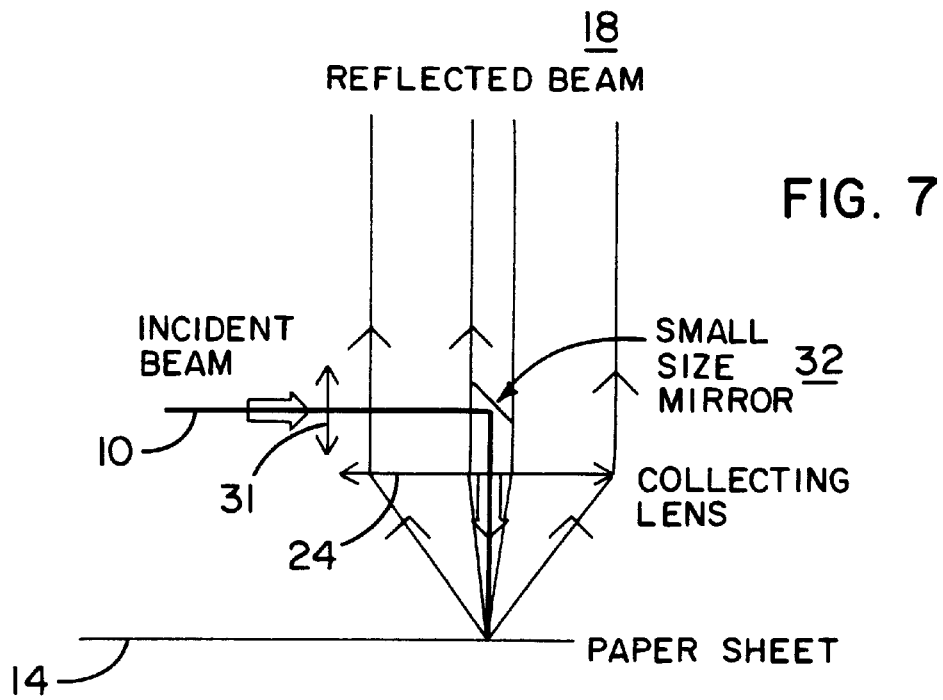
FIG. 7 is a schematic of a large lens and small mirror for an optical head.

For paper products in which no special polarization of the incident beam 10 is required, the optical head 20 shown in FIG. 7 may be used. Referring to FIG. 7, incident beam 10 is focused by converging lens 31 and reflected onto the paper web 14 by a small mirror 32. The light backscattered from the paper web 14 is collected and collimated by a large converging lens 24. Preferably lens 24 has a small f-number (focal length/effective diameter), which allows maximization of the light collection from the paper web 14.

Figure 8:
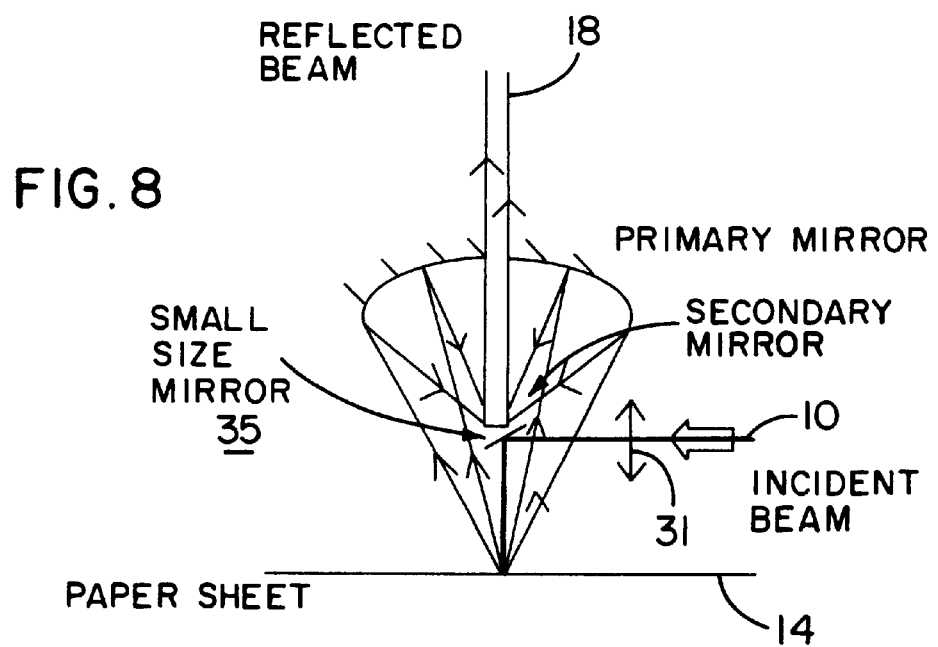
FIG. 8 is a schematic of a Cassegrain objective and small mirror for an optical head.

Another optical head 20 is shown in FIG. 8. Referring to FIG. 8, incident beam 10 is focused by a converging lens 31, then reflected by a small mirror 35 onto paper web 14. The incident beam has its focal point on or near the surface of the paper web 14. The light backscattered by the paper web 14 is collected and collimated by a Cassegrain type objective.

Cassegrain objective includes primary mirror 33 and secondary mirror 34. Primary mirror 33 has a hole in its center and reflects back the collected light towards the secondary mirror 34, which focuses the collected light into a collimated beam 18 traveling back through the hole in primary mirror 33. The quantity of light that can be collected by this objective is large compared to other optical heads, which makes this optical head configuration particularly useful in photorefractive interferometer 100.

The optical heads shown in FIGS. 7 and 8 are preferred for use with paper webs having a depolarizing surface since these configurations are not polarization dependent.

Figure 13A:
FIGS. 13A, 13B, 13C are views from an optical axis (13A), cross-section (13B) and volume (13C) of converging lenses that may be used in an optical head.
Figure 13A:
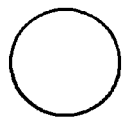
Figure 13A:
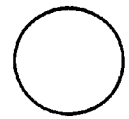
Figure 13B:
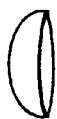
Figure 13B:
Figure 13B:
Figure 13C:
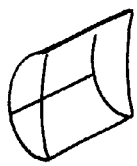
Figure 13C:
Figure 13C:
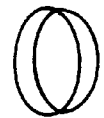

Various lenses can be used in each of the optical heads described with respect to FIGS. 5, 6, 7 and 8. Examples of such lenses include cylindrical plano-convex, spherical plano-convex and spherical meniscus. FIG. 13A shows the view from the optical axis for each such lens; FIG. 13B shows the cross-section view; and FIG. 13C shows the volume view of each lens.

Figure 9:
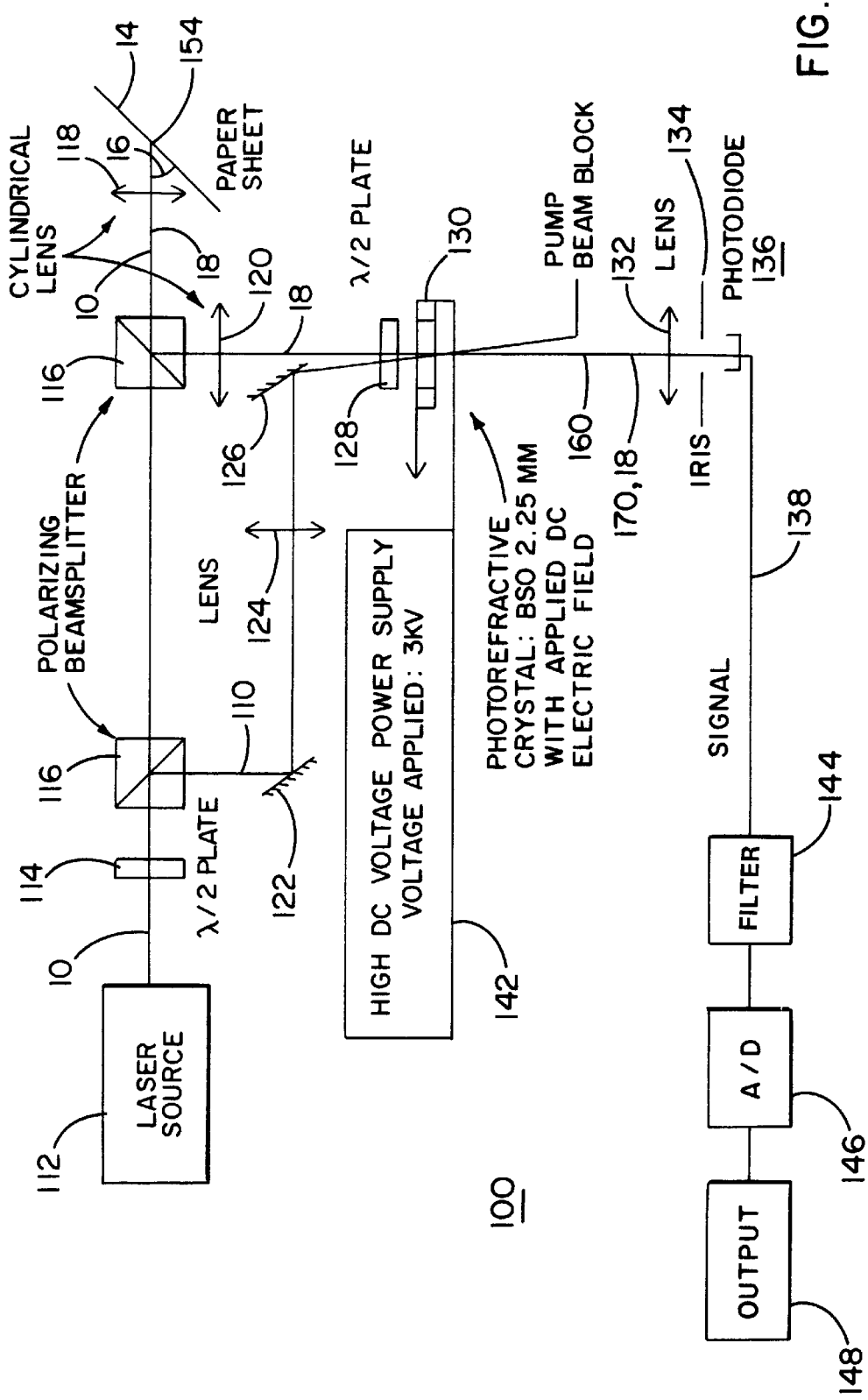
FIG. 9 is a schematic of a setup for a two-wave mixing photorefractive interferometer.

Referring to FIG. 9, a preferred apparatus for non-contact measurement of ultrasonic waves in a moving paper web is shown therein and generally referred to by number 100. Other configurations of a photorefractive interferometer apparatus may also be used. Apparatus 100 includes laser source 112 which provides incident beam 10 to halfwave plate 114, then to polarizing beamsplitter 116. Incident beam 10 is then focused by lens 118, which is preferably a cylindrical lens, onto moving paper web 14. Reflected light 18 is focused in cylindrical lens 118, then passes through polarizing beamsplitter 116 where it is directed to cylindrical lens 120. Reflected light 18 then passes through half wave plate 128 before it is provided to photorefractive crystal 130.

Note that the optical head provides the incident beam 10 and collected beam 18 at an angle 16 to the surface of the moving paper. Preferably this angle is about 45 degrees. Beamsplitter 116 is used to separate the incident beam 10 from the collected beam 18. Halfwave plates are used to change the intensity/power of the incident beam to the reference beam.

Beamsplitter 116 provides a pump beam 110 which is reflected by mirror 122, focused by lens 124 and reflected by mirror 126 onto photorefractive crystal 130. Pump beam 110 also goes through halfwave plate 128 before it is provided to the photorefractive crystal 130. Lens 124 must have a focal length sufficiently short so that the focal point is well before the photorefractive crystal 130 and the pump beam 110 impinges the entire input surface of the photorefractive crystal 130.

Crystal 130 is preferably a BSO having a thickness of 2.25 millimeters when the photorefractive interferometer is used on static paper. To enhance signal to noise ratio, a 3 kV DC signal is applied to the crystal 130 from the power supply 142. Pump beam 110 and collected (signal) beam 18 interfere inside the photorefractive crystal 130 and form a grating. This grating diffracts the pump beam 110 into a reference beam 170 having a wavefront similar to the one of the collected beam 18. Reference beam 170 and collected (signal) beam 18 then interfere a second time in photodiode 136. The two beams 170, 18 are focused by lens 132 before they are applied to photodiode 136 through iris 134. Photodiode 136 generates an electrical signal 138 representative of the ultrasonic signal which is applied to high pass filter 144 (preferably filters from 13 kHz to 6 MHz) before it is applied to analog to digital board 146 (preferably samples at 10 MHz). The output of A/D board 146 may be applied to a suitable display 148 (printer, oscilloscope, or computer monitor) for viewing and analysis of the speeds of ultrasonic waves in the paper and thus of the paper's properties. Alternatively, the output can be used in a feedback loop to control operation of the moving paper web (not shown).

The incident beam 10 is circular and focused by cylindrical lens 118 along the horizontal direction. The focused detection spot 154 is a vertical line of about 2 millimeters in length and less than half a millimeter in width. The apparatus 100 is sensitive to ultrasonic waves propagating in the direction perpendicular to the focused detection spot. Line detection presents a significant advantage over point detection since the power impinging the paper can be increased without burning it.

Apparatus 100 is especially useful for testing static linerboard due to linerboard's low damage threshold giving a low collected power and small signal to noise ratio. The polarization of the incident beam onto the paper is linear horizontal and not circular. The rough surface of the linerboard depolarizes much of the backscattered light. A quarterwave plate before the focusing lens 118 is not necessary since the polarizing beamsplitter 116 will select only the vertically polarized speckles for the signal beam.

If only one cylindrical lens 118 is used to focus both the incident beam and the backscattered light, the backscattered light collected is a line. The backscatter line must be refocused by lens 120 along the direction of the line 154 onto the surface of the photorefractive crystal 130 to interfere more efficiently with the pump beam 110. Phase information (i.e. the ultrasonic displacements) are written by the photorefractive effect on the collected beam 18 and diffracted reference beam 170 after they have gone through the crystal 130. This provides detection of the ultrasonic phase shift by interference between these two beams (18 and 170) on photodiode 136.

Figure 10A:
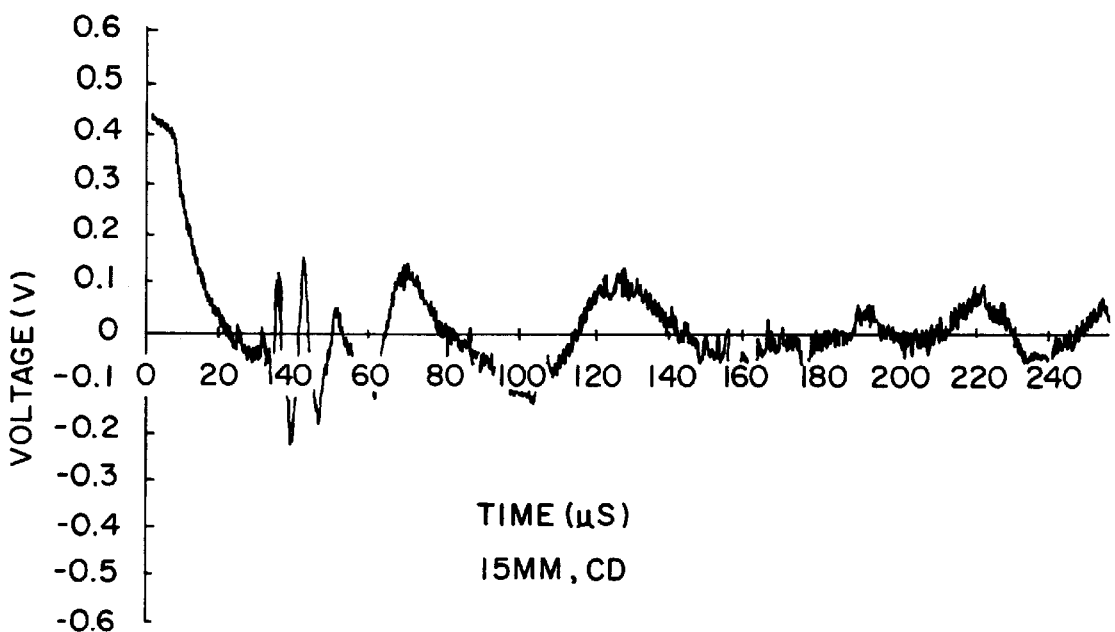
FIGS. 10A–10D are measurements of laser generated waves travelling along the cross direction of 42 pound linerboard using the photorefractive interferometer of FIG. 9.
Figure 10B:
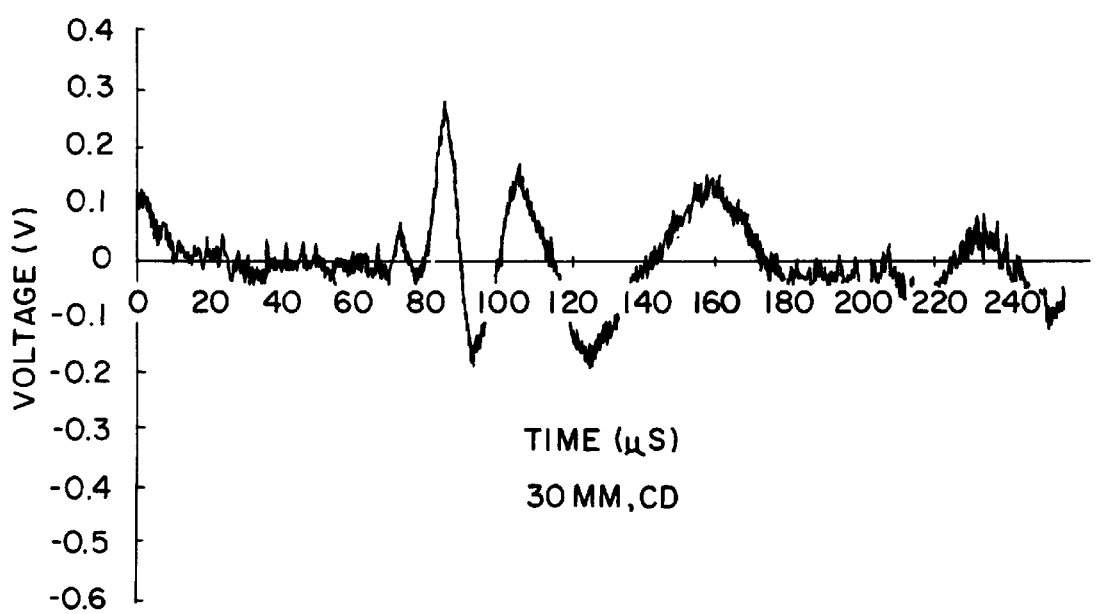
Figure 10C:
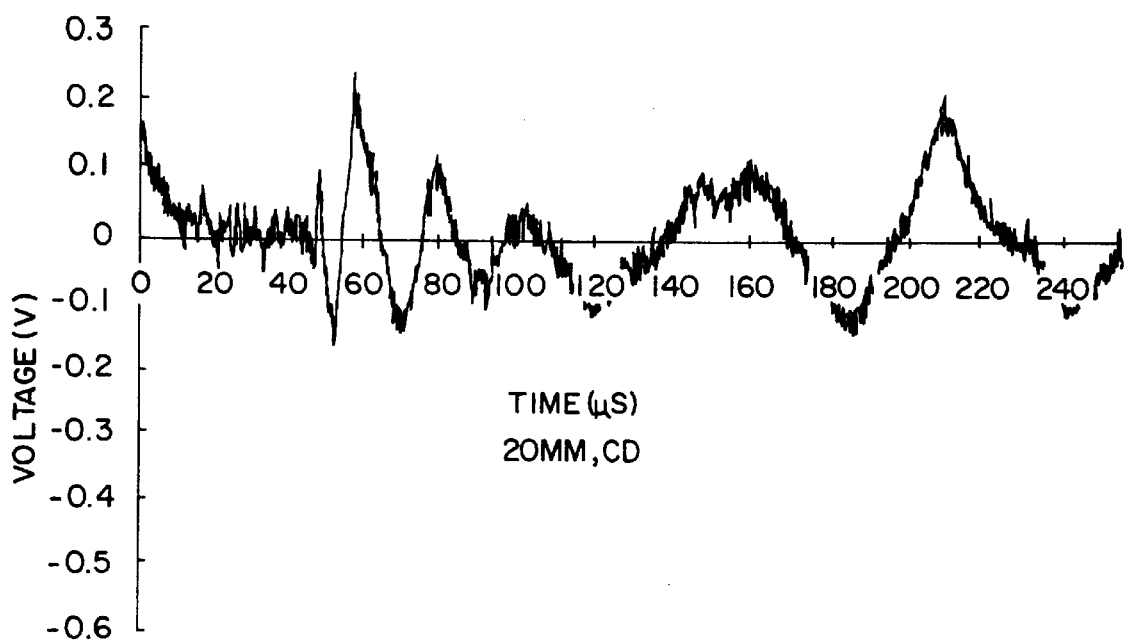
Figure 10D:
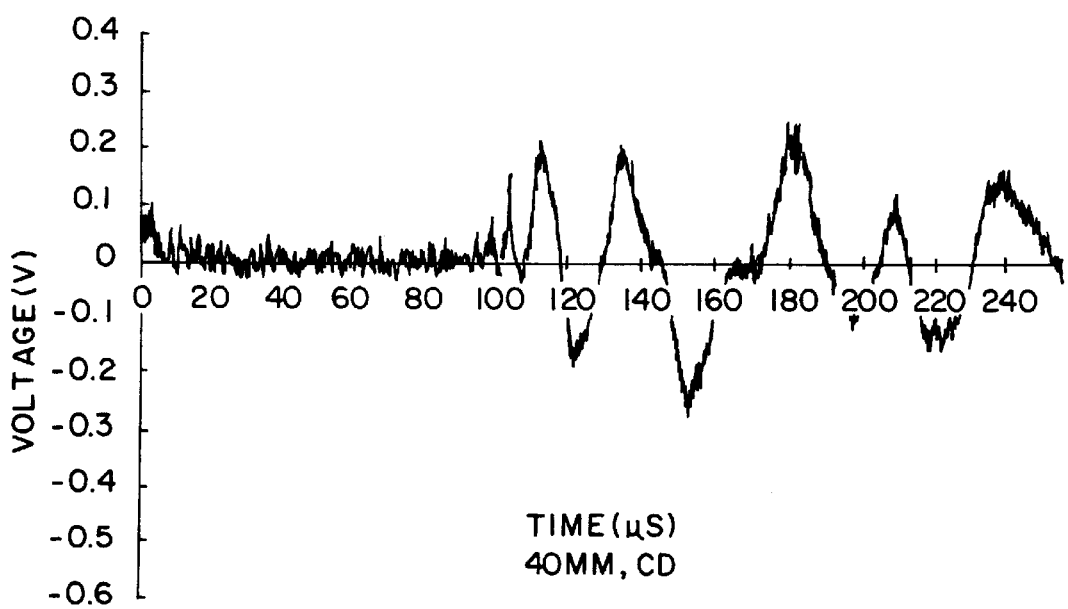
Figure 11A:
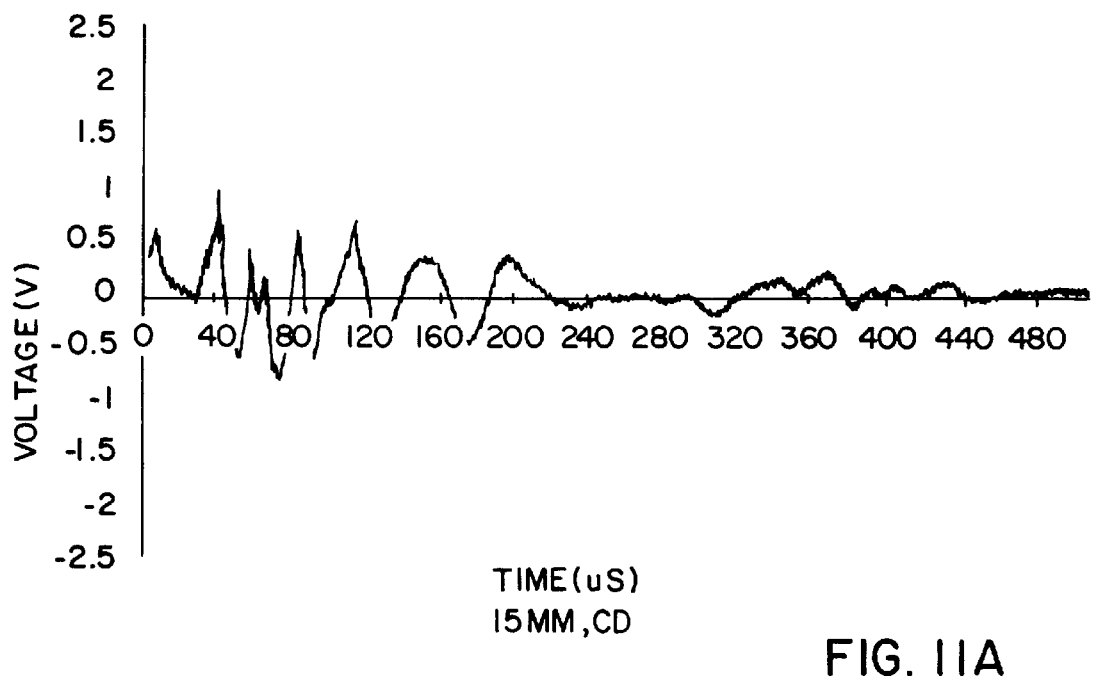
FIGS. 11A–11D are measurements of laser generated waves travelling along the cross direction of copy paper using the photorefractive interferometer of FIG. 9.
Figure 11B:
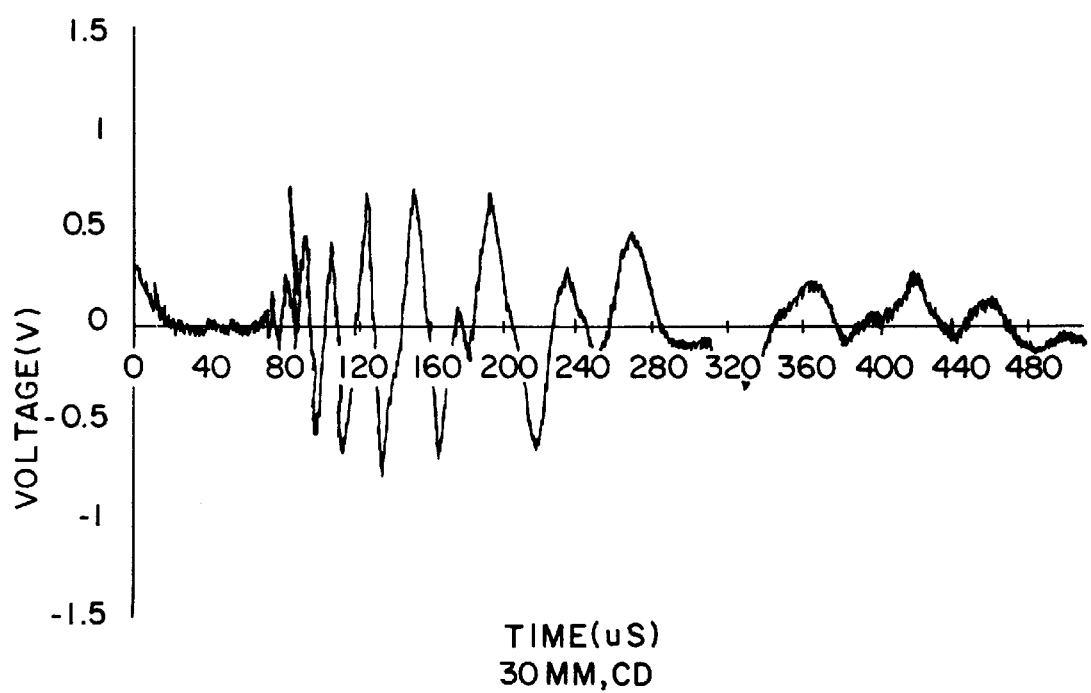
Figure 11C:
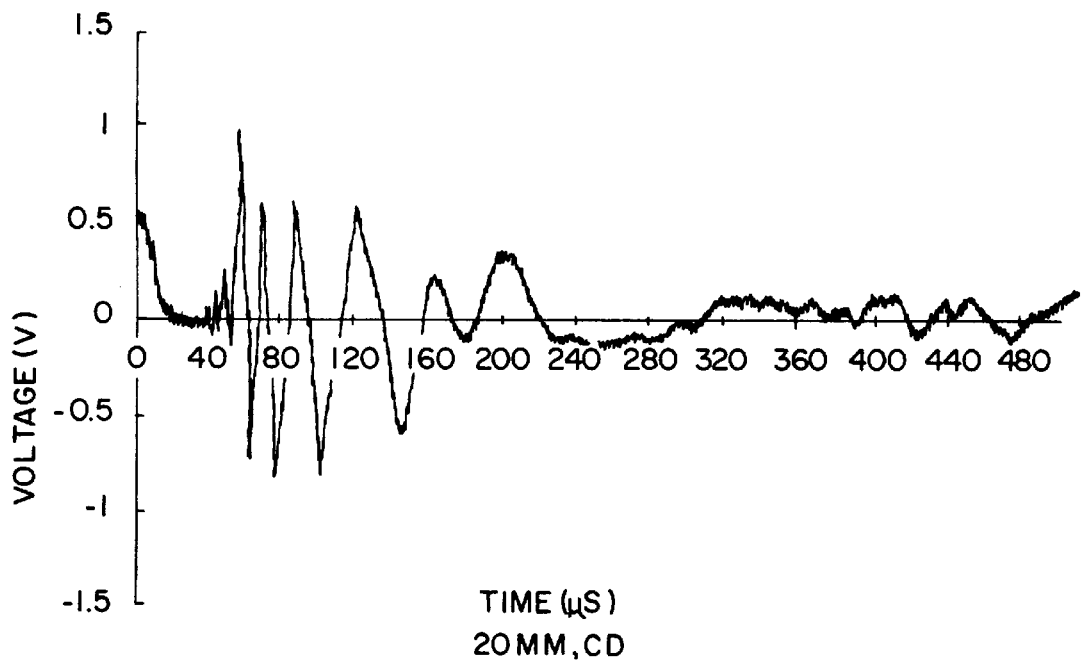
Figure 11D:
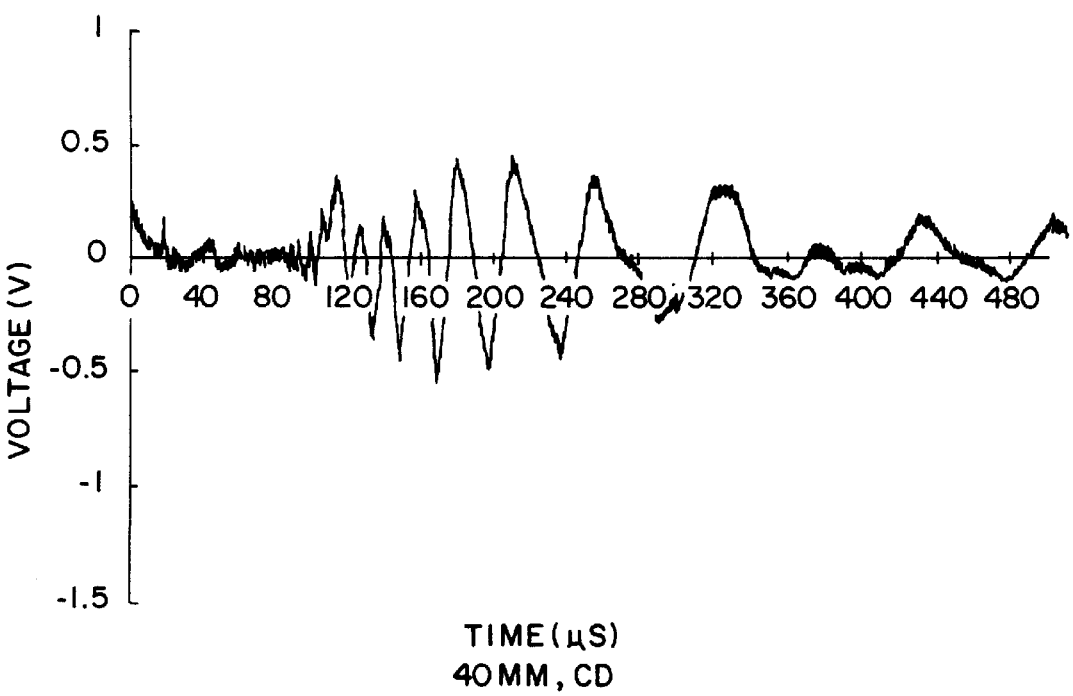
Figure 12A:
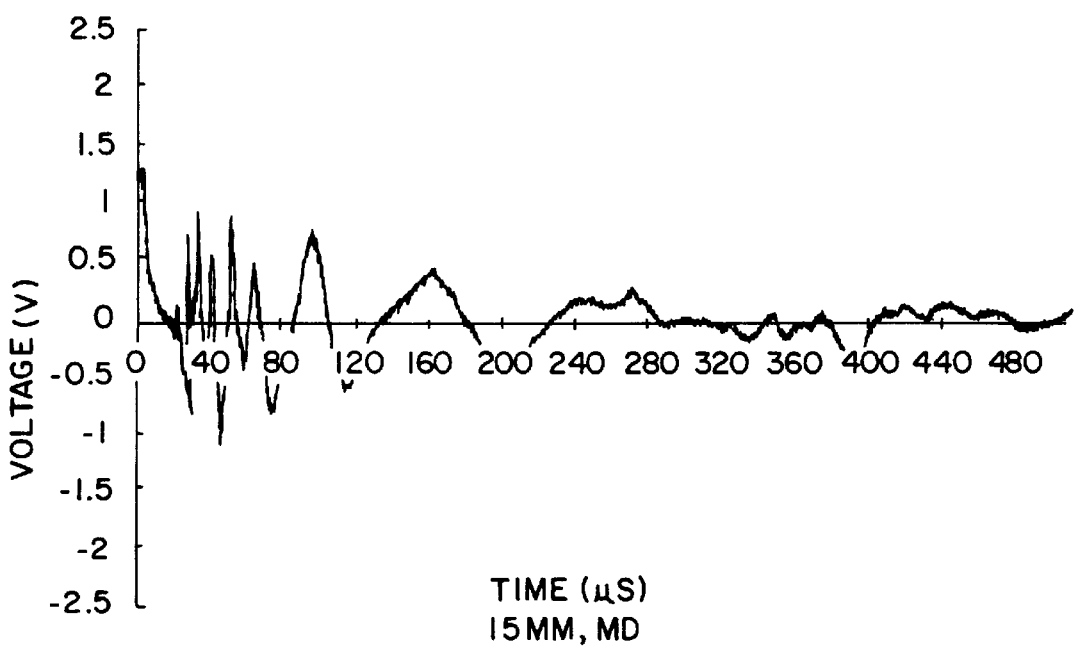
Figure 12B:
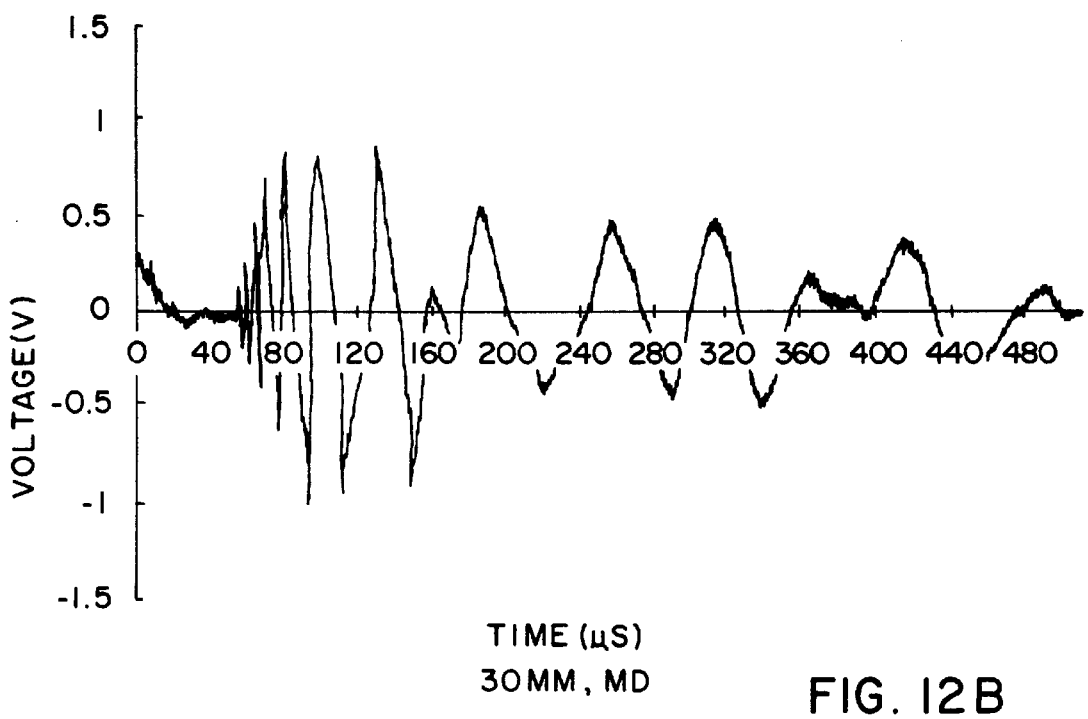
Figure 12C:
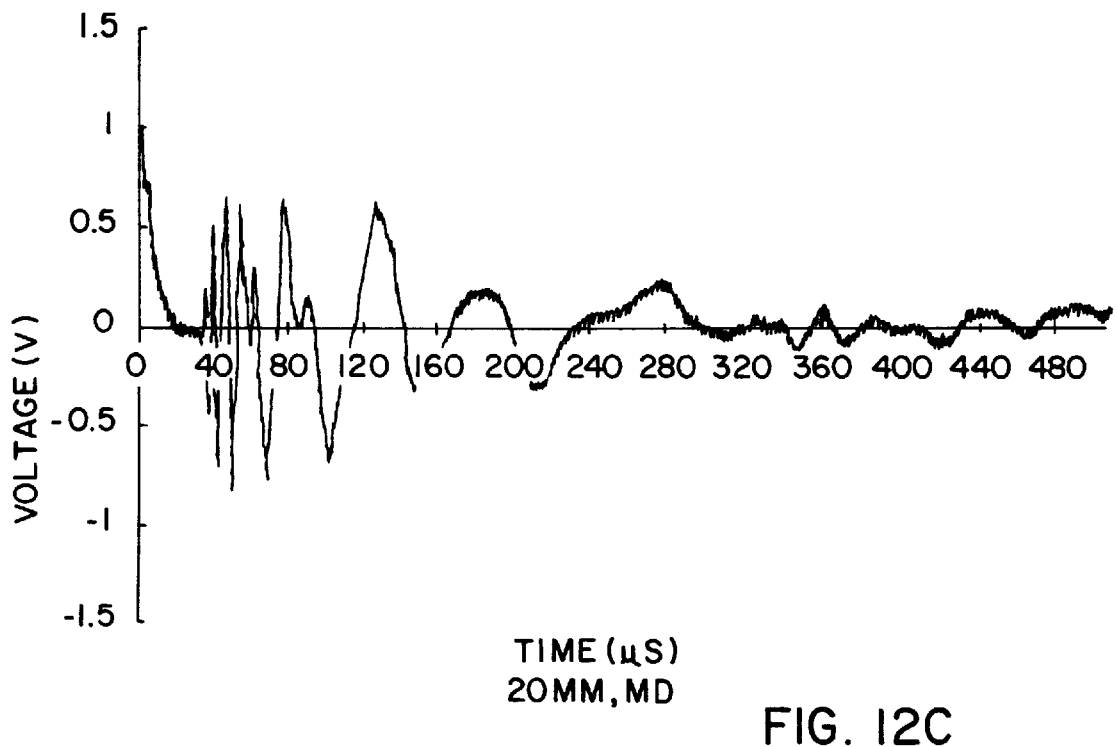
Figure 12D:
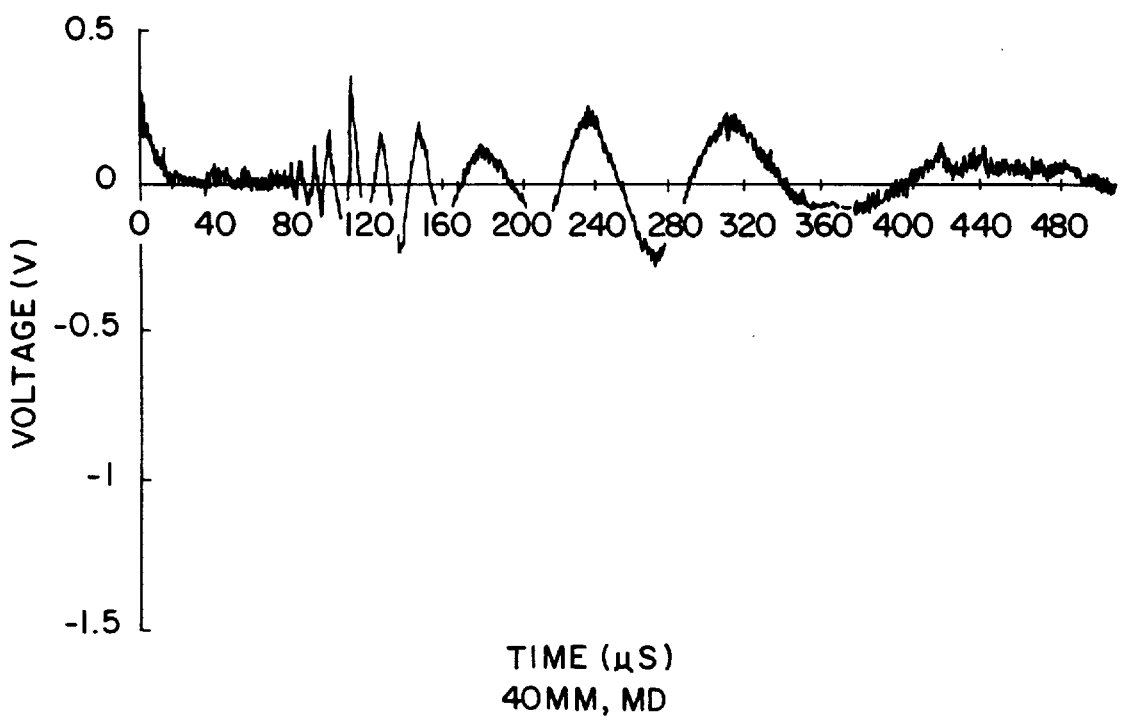

Example results using the apparatus 100 of FIG. 9, wave and incidence angle 16 of 45 degrees, are shown in FIGS. 10A–10D. Laser generated waves travelling in the cross direction (CD) of the paper were focused onto 42 pound linerboard. FIG. 10A shows the resultant displacement waveforms $A_0$ and $S_0$ detected 15 millimeters apart from the laser generation spot. The $S_0$ waveform is the first order symmetric Lamb wave and the $A_0$ is the first order antisymmetric Lamb wave. $S_0$ is also an in-plane waveform and $A_0$ is an out-of-plane waveform. The detection of both waves proves that the photorefractive interferometer 100 using a single optical head in which the incident beams and reflection beams are substantially coaxial can detect in-plane and out-of-plane ultrasonic waves. FIGS. 10B, 10C and 10D show the resultant waveform detected at 20 millimeters, 30 millimeters and 40 millimeters, respectively. Because of the saturation of the photodiode 136, the $S_0$ waveform does not come out of the noise. All of the data in FIGS. 10A–10D is the result of a single shot for the generation beam of 40.2 milliJoules. It can be seen that even at long distances between generation and detection points (i.e., 40 millimeters), the $A_0$ waveform remains visible.

FIGS. 11A, 11B, 11C and 11D show the resultant waveform $A_0$ from laser generated waves traveling in the cross direction of a moving web of copy paper at 15 millimeters, 20 millimeters, 30 millimeters and 40 millimeters from the excitation point, respectively. All data are also from single shot measurements. The $S_0$ waveform is visible, but has a small amplitude compared to $A_0$, which is expected. Here the dispersive nature of $A_0$ is apparent.

FIGS. 12A, 12B, 12C and 12D show the resultant waveform $A_0$ from laser generated waves traveling in the machine direction (MD) of a moving web of copy paper at 15 millimeters, 20 millimeters, 30 millimeters and 40 millimeters from the excitation point, respectively. All data are also from single shot measurements from an incident pulse of 40.2 mJ. The $S_0$ waveform is clearly visible at longer generation-detection distances because the saturation of the photodiode 136 by the generation pulse at 1064 nm is not as strong. There is less 1064 nm parasitic light collected by the detection optics when the two spots are further apart and the arrival time of the $S_0$ wave starts to be out of the saturation zone in the first 10 microseconds. The waveforms travelling along the MD are similar in shape to those along the CD, which is expected. The times of flight are different because the elastic constants are different along the MD compared to the CD, which is expected. There is a sooner time of arrival of both the $S_0$ and $A_0$ waves on the measurements along the MD compared to the CD.

A photorefractive interferometric probe, due to the large size of the crystal (a few mm) putting the two waves (signal and reference) into the same direction, and due to the dynamic writing of the grating, which match the signal and pump beams wavefronts, is expected to have a significant étendue. Its étendue is expected to be much greater than that of a Mach-Zehnder interferometer, and of the same order of magnitude of a Fabry-Pérot interferometer. But the étendue will result from the optical head. Thus, this great étendue should result in a device much less dependent of the surface roughness and of the sheet fluttering than a conventional Mach-Zehnder interferometer. This characteristic is of great interest for investigations on paper products, which are materials known as having a very scattering surface.

The generation of the ultrasonic waves detected by the photorefractive probe on paper products could (but would not be obliged to) be done by a pulsed laser or contact transducers, or air-coupled transducers.

While there has been illustrated and described a particular embodiment of the present invention, it will be appreciated that numerous changes and modifications will occur to those skilled in the art, and it is intended in the appended claims to cover all those changes and modifications which followed in the true spirit and scope of the present invention.

What is claimed is:

1. An apparatus for non-contact measurement of ultrasonic waves in a moving paper web, comprising;
    a laser source for providing an incident beam and a pump beam having a coherence length sufficient for use in interferometry;
    an optical head for focusing the incident beam onto the surface of the paper and for collecting the resulting laser speckles scattered from the paper over a solid angle into a reflected beam, wherein the incident beam and the reflected beam are substantially coaxial and travel through the optical head with an angle of incidence for detecting ultrasonic waves moving in plane with the paper web and in directions outside the plane of the paper web;
    a photorefractive crystal for receiving the pump beam and the reflected beam, wherein the pump beam and the reflected beam interfere creating a grating for diffracting the pump beam into a reference beam having a wavefront substantially the same as the wavefront of the reflected beam; and
    apparatus for causing the reflected beam and the reference beam to interfere and for converting phase variations of the reflected beam caused by the ultrasonic waves into an electrical signal;
    wherein the electrical signal represents ultrasonic movement in the paper web.

2. The apparatus of claim 1 wherein the apparatus for converting phase variations comprises a photodiode.

3. The apparatus of claim 1 wherein the apparatus for converting phase variations comprises the photorefractive crystal.

4. The apparatus of claim 1 further comprising a high voltage source for providing a high voltage to the photorefractive crystal.

5. The apparatus of claim 1 wherein the laser source generates a continuous wave beam.

6. The apparatus of claim 1 wherein the laser source generates a pulsed beam.

7. The apparatus of claim 1 wherein the photorefractive crystal comprises a semiconductor material.

8. The apparatus of claim 7 wherein the semiconductor material is selected from the group consisting of GaAs, GaAs:Cr, InP:Fe, CdTe:V.

9. The apparatus of claim 1 wherein the optical head is configured to focus the incident beam onto a spot on the surface of the paper web, wherein the spot is shaped as a line.

10. The apparatus of claim 1 wherein the optical head comprises a polarization separator, a quarterwave plate and a focusing and collecting lens.

11. The apparatus of claim 10 wherein the collecting lens is selected from the group of cylindrical plano-convex, spherical plano-convex and spherical meniscus.

12. The apparatus of claim 1 wherein the optical head comprises a polarization separator and a focusing and collecting lens.

13. The apparatus of claim 12 wherein the collecting lens is selected from the group of cylindrical plano-convex, spherical plano-convex and spherical meniscus.

14. The apparatus of claim 1 wherein the optical head comprises a mirror, a focusing lens and a collecting lens.

15. The apparatus of claim 14 wherein each of the focusing lens and the collecting lens is selected from the group of cylindrical plano-convex, spherical plano-convex and spherical meniscus.

16. The apparatus of claim 1 wherein the optical head comprises a Cassegrain objective, a lens and a mirror.

17. The apparatus of claim 16 wherein the Cassegrain objective comprises a primary mirror having a hole and a secondary mirror.

18. A method for non-contact measurement of ultrasonic waves in a moving paper web, comprising;
    providing an incident laser beam having a temporal coherence length sufficient for use in interferometry;
    providing a pump beam coherent with the incident beam;
    focusing the incident beam into a line shaped spot onto the surface of the paper;
    collecting the resulting laser speckles scattered from the paper over a solid angle into a reflected beam with an angle of incidence for detecting ultrasonic displacements in plane with the paper web and substantially perpendicular to the plane of the paper web, wherein the reflected beam is substantially coaxial with the incident beam and wherein the phase of the collected light is shifted by movement of the paper web caused by said ultrasonic waves therein;
    causing the pump beam and the reflected beam to interfere in a photorefractive crystal forming an index grating for diffracting the pump beam into a reference beam having a wavefront substantially the same as the wavefront of the reflected beam; and
    converting phase variations of an optical interference signal between the reference beam and the reflected beam to an electrical signal;
    wherein the electrical signal represents ultrasonic movement in the paper web.

19. The method of claim 18 wherein ultrasonic waves in said moving web are generated by a pulsed laser generation beam, and further comprising:
    triggering an acquisition of the electrical signal when said pulsed generation beam impinges a surface of the moving paper web;
    calculating speeds of ultrasonic waves from said electrical signals; and
    converting said speeds into mechanical properties of the moving web.

20. An apparatus for non-contact measurement of ultrasonic waves in a static paper web, comprising;
    a laser source for providing an incident beam and a pump beam having a coherence length sufficient for use in interferometry;
    an optical head for focusing the incident beam onto the surface of the paper and for collecting the resulting laser speckles scattered from the paper over a solid angle into a reflected beam with an angle of incidence for detecting ultrasonic waves moving in plane with the paper web and in directions outside the plane of the paper web, wherein the incident beam and the reflected beam are substantially coaxial;
    a photorefractive crystal for receiving the pump beam and the reflected beam, wherein the pump beam and the reflected beam interfere creating a grating for diffracting the pump beam into a reference beam having a wavefront substantially the same as the wavefront of the reflected beam; and apparatus for causing the reflected beam and the reference beam to interfere and for converting phase variations of the reflected beam caused by the ultrasonic waves into an electrical signal;

wherein the electrical signal represents ultrasonic movement in the paper web.

21. The apparatus of claim 20 wherein the photorefractive crystal comprises a Sillenite material.

22. The apparatus of claim 21 wherein the Sillenite material is selected from the group consisting of $Bi_{12}SiO_{20}$ (BSO) $Bi_{12}GeO_{20}$ (BGO) and $Bi_{12}TiO_{20}$ (BTO).

23. The apparatus of claim 1 wherein said optical head focuses the incident beam with an angle of incidence of approximately 45 degrees for detecting in-plane and out-of-plane displacements of the ultrasonic waves propagating in the paper web.

24. The apparatus of claim 1 wherein said optical head focuses the incident beam with an angle of incidence to the plane of the paper web for detecting ultrasonic waves moving in-plane with the paper web and in directions substantially normal to the plane of the paper web.

25. The apparatus of claim 20 wherein the incident beam and the reflected beam travel through the same optical head.

* * * * *